(12) United States Patent
Travkina et al.

(10) Patent No.: US 11,077,049 B2
(45) Date of Patent: Aug. 3, 2021

(54) LONG-WEARING GLOSSY LIPSTICK

(71) Applicant: New Avon LLC, New York, NY (US)

(72) Inventors: Irina Travkina, River Edge, NJ (US); Sen Yang, Highland, NY (US)

(73) Assignee: New Avon LLC, New York, NY (US)

( * ) Notice: Subject to any disclaimer, the term of this patent is extended or adjusted under 35 U.S.C. 154(b) by 0 days.

(21) Appl. No.: 14/361,765

(22) PCT Filed: Feb. 26, 2014

(86) PCT No.: PCT/US2014/018649
§ 371 (c)(1),
(2) Date: May 30, 2014

(87) PCT Pub. No.: WO2014/158599
PCT Pub. Date: Oct. 2, 2014

(65) Prior Publication Data
US 2015/0297493 A1  Oct. 22, 2015

Related U.S. Application Data

(60) Provisional application No. 61/781,176, filed on Mar. 14, 2013.

(51) Int. Cl.
| | | |
|---|---|---|
| *A61K 8/81* | (2006.01) | |
| *A61K 8/34* | (2006.01) | |
| *A61Q 1/06* | (2006.01) | |
| *A61K 8/73* | (2006.01) | |
| *A61K 8/365* | (2006.01) | |
| *A61K 8/85* | (2006.01) | |
| *A61K 8/92* | (2006.01) | |

(52) U.S. Cl.
CPC ............ *A61K 8/8111* (2013.01); *A61K 8/342* (2013.01); *A61K 8/365* (2013.01); *A61K 8/731* (2013.01); *A61K 8/85* (2013.01); *A61K 8/922* (2013.01); *A61Q 1/06* (2013.01); *A61K 2800/30* (2013.01); *A61K 2800/43* (2013.01); *A61K 2800/592* (2013.01)

(58) Field of Classification Search
None
See application file for complete search history.

(56) References Cited

U.S. PATENT DOCUMENTS

| | | | |
|---|---|---|---|
| 2002/0164297 A1 | 11/2002 | Ferrari et al. | |
| 2004/0234612 A1* | 11/2004 | Blin | A61K 8/375 424/489 |
| 2006/0019848 A1* | 1/2006 | Luo | A61K 8/064 510/130 |
| 2008/0110372 A1 | 5/2008 | Hollman et al. | |
| 2008/0299057 A1 | 12/2008 | Lin | |
| 2010/0291015 A1* | 11/2010 | Barba | A61K 8/02 424/64 |
| 2011/0021699 A1 | 1/2011 | Fritschins et al. | |
| 2011/0150792 A1* | 6/2011 | Shao etal. | 424/59 |

FOREIGN PATENT DOCUMENTS

| | | |
|---|---|---|
| CN | 1387836 A | 1/2003 |
| CN | 1535672 A | 10/2004 |
| CN | 102228412 A | 11/2011 |
| GB | 2376277 A | 12/2002 |

\* cited by examiner

*Primary Examiner* — H. Sarah Park
(74) *Attorney, Agent, or Firm* — King & Spalding

(57) ABSTRACT

Cosmetic compositions having durable gloss, such as cosmetic lipcolors, are provided. The compositions comprise a gel formed from a cellulosic polymer and a polar oil, a non-polar film-forming agent, polyhydroxystearic acid, and optionally one or more pigments. The compositions may have one or more properties selected from long-wear, oil transfer resistance, water transfer resistance, comfort, and durable shine.

7 Claims, No Drawings

LONG-WEARING GLOSSY LIPSTICK

RELATED APPLICATION

This application claims priority benefit, under the national stage entry under 35 U.S.C. 371 of International Application No. PCT/US14/18649, filed on Feb. 26, 2014 the contents of which application are hereby incorporated by reference in their entirety. This patent application claims priority to U.S. Patent Application Ser. No. 61/781,176, filed on Mar. 14, 2013. The entirety of the aforementioned application is incorporated herein in its entirety by reference.

FIELD OF INVENTION

The invention relates generally to wear resistant, durable lipcolor cosmetics that provide a high degree of color and gloss. More particularly, the invention relates to lipcolor cosmetics having high pigment loads that exhibit superior long wearing shine and comfort.

BACKGROUND OF THE INVENTION

It has long been considered desirable to provide cosmetic lipcolor products, such as lipstick and glosses, which impart a shiny finish to the lips. Conventionally, cosmetic lip products comprise pigments dispersed in a base of fats or oils with various waxes added to provide the desired consistency of the product. Lip glosses are often liquid to semi-solid in consistency to provide the fluid, smooth consistency and high payoff desired by consumers.

However, the shiny finish and smooth aesthetics provided by the conventional oily base comes at the cost of durability. A notable disadvantage of traditional lipcolor products is the lack of wear the consumer experiences, resulting in fading, feathering, and diminished gloss, all of which require re-application within a short period of time. Moreover, lipcolors tend to accumulate in fine creases of the lips and surrounding skin leading to an undesirable "feathering" effect. Similarly, the oils may cause the color to migrate or bleed beyond the boundaries of the lips resulting in a halo effect.

To date, efforts to provide durable, long-wearing, lip products have met with only moderate success. Commercial long-wear lip products have been reported to be uncomfortable to wear and may have a drying effect on the lips. Further, the long-lasting shiny finish which is sought in lip gloss products has proven difficult to replicate in such products.

There is an ongoing need for cosmetic compositions, which may be used, for example, as lip gloss compositions, that combine high shine, fluidity, and smooth consistency with wear resistance and vibrant color. It is therefore an object of the present invention to provide cosmetic compositions, such as lipstick and lip gloss, which meet one or more of these requirements.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, the present invention provides methods and compositions for forming a durable glossy deposit on a human integument, including hum skin, and in particular the lips. In one aspect of the invention, compositions are provided comprising (1) from about 1% to about 50% (e.g., about 30% to about 40%) by weight of a polar oil (e.g., octyldodecanol); (2) from about 0.3% to about 7% by weight of a cellulosic polymer (e.g., ethyl cellulose) capable of forming a gel with said polar oil; (3) from about 1% to about 10% by weight of a non-polar film-forming polymer (e.g., polybutene); (4) from about 0.1% to about 0.5% by weight of polyhydroxystearic acid; and (5) from about 1% to about 35% (e.g., about 8% to about 12%) by weight pigments. The compositions may or may not be substantially anhydrous. The compositions may or may not be substantially free of wax. The compositions may or may not be substantially free of silicone oils.

The cosmetic composition may be capable of imparting durable shine to the lips, by which is meant that the film has high gloss over a prolonged period of time (e.g., the gloss diminishes by less than 25% over a period of one hour or more). In one embodiment, the composition loses less than 10% of its gloss over a 3 hour period.

In some implementations, the gel will comprises a polar oil in an amount from about 25% to about 45%, such as a fatty alcohol, and in particular a branched fatty alcohol (e.g., octyldodecanol), or an ester oil, gelled with a cellulosic in an amount from about 1% to about 4%, such as a cellulose ether, and notably a water-insoluble cellulose ether such as ethyl cellulose. The non-polar film-forming polymer may advantageously comprise a polyolefin polymer which increases shine, such as polybutene.

In another aspect, the cosmetic composition is prepared from a pre-grind of pigments and polyhydroxystearic acid (e.g., formed by mixing said pigments with said polyhydroxystearic acid under shear). It is believed that a composition made using such a pre-grind will exhibit superior gloss and accentuated pigment development as compared to an otherwise identical composition in which pigments and polyhydroxystearic acid are added directly to the composition without first forming a pre-grind.

In another aspect of the invention, compositions are provided comprising (1) from about 25% to about 45% by weight of a polar oil comprising octyldodecanol; (2) from about 0.3% to about 7% by weight of ethyl cellulose capable of forming a gel with said polar oil; (3) from about 1% to about 10% by weight of polybutene film forming polymer; (4) from about 0.1% to about 0.5% by weight of polyhydroxystearic acid; and (5) from about 1% to about 35% by weight pigments. The compositions may or may not be substantially anhydrous. The compositions may or may not be substantially free of wax. The compositions may or may not be substantially free of silicone oils. It is typically capable of imparting durable shine and providing a long-wearing, transfer resistant glossy film on the lips.

In another aspect of the invention, a method of manufacturing a cosmetic lip composition capable of imparting durable shine and providing a long-wearing, transfer resistant glossy film on the lips is provided. The method comprises the steps of forming a pigment pre-grind of a pigment with polyhydroxystearic acid (e.g., by mixing under shear or grinding force); forming a gel from a cellulosic polymer and a polar oil; and mixing the pigment pre-grind, the gel, a non-polar film-forming agent, and optionally additional ingredients, together under high shear to form a cosmetic lip composition. It is believed that such a method results in a lipcolor composition with higher gloss and accentuated pigment development than an otherwise comparable composition in which the pigment and polyhydroxystearic acid are not mixed in a pre-grind.

In another aspect of the invention, a method is provided for forming a long-wearing film, a comfortable film, and/or a glossy film on the lips comprising applying to the lips a composition according to the invention. Additionally, such films should exhibit oil and water transfer resistance when applied to lips. In a related method, a film is formed on the lips, which is characterized as having high durable shine. In another method, a film is formed on the lips that has a reduced propensity to bleed or feather as compared to cosmetic compositions which lake the gelling agent.

These and other aspects of the present invention will become apparent to those skilled in the art after a reading of the following detailed description of the invention, including the appended claims.

DETAILED DESCRIPTION

All amounts provided in terms of weight percentage are relative to the entire composition unless otherwise stated. Unless otherwise provided, the term "alkyl" is intended to embrace straight-chained, branched, or cyclic hydrocarbons, particularly those having from one to 20 carbon atoms, and more particularly $C_{1-18}$ or $C_{1-16}$ or $C_{1-12}$ or $C_{1-10}$ or $C_{1-6}$ hydrocarbons. The term "lower alkyl" includes, without limitation methyl, ethyl, propyl, isopropyl, butyl, n-butyl, iso-butyl, tert-butyl, pentyl, neo-pentyl, amyl, and hexyl, including cyclized analogues thereof. Unless otherwise provided, the term "alkenyl" is intended to embrace straight-chained, branched, or cyclic hydrocarbons, particularly those having from one to 20 carbon atoms, and more particularly $C_{1-18}$ or $C_{1-16}$ or $C_{1-12}$ or $C_{1-10}$ or $C_{1-6}$ hydrocarbons, which may include one, two, three, or more unsaturated carbon-carbon bonds, which may be in the E or Z configuration.

The compositions of the invention are useful for application to the human integumentary system, including, skin, lips, nails, hair, and other keratinous surfaces. As used herein, the term "keratinous surface" refers to keratin-containing portions of the human integumentary system, which includes, but is not limited to, skin, lips, hair (including eyebrows and eyelashes), and nails (toenails, fingernails, cuticles, etc.) of mammalians, preferably humans. A "keratin fiber" includes hair of the scalp, eyelashes, eyebrows, facial hair, and body hair such as hair of the arms, legs, etc.

The compositions generally comprise (1) from about 1% to about 50% (e.g., about 1-10%, about 10-20%, about 30-40%, or about 40-50%) by weight of a polar oil; (2) from about 0.3% to about 7% (e.g., about 0.1-1%, or about 1%-2%, or about 2-3%, or about 3-4%, or about 4-5%, or about 5-6%, or about 6-7%) by weight of a cellulosic polymer capable of forming a gel with the polar oil; (3) from about 1% to about 10% (e.g., about 1%-2%, or about 2-3%, or about 3-4%, or about 4-5%, or about 5-6%, or about 6-7%, or about 7-8%, or about 8-9%, or about 9-10%) by weight of a non-polar film-forming polymer; (4) from about 0.1% to about 0.5% (e.g., about 0.1-0.2%, or about 0.2-0.3%, or about 0.3-0.4%, or about 0.4-0.5%) by weight of polyhydroxystearic acid; and (5) from about 1% to about 35% (e.g., about 8% to about 12%) by weight pigments.

The polar oil may comprise a fatty alcohol or an ester oil. Suitable fatty alcohols include any alcohol of the form $CH_3(CH_2)nCH_2OH$, where n is an integer from 6-26 (or from 8-20, or from 10-18) and unsaturated analogs thereof. Examples include, without limitation, cetyl, lauryl, stearyl, linoleyl and oleyl alcohols. In some embodiments, branched fatty alcohols are used. Branched fatty alcohols may be dimer alcohols. In some embodiments, branched fatty alcohols will have the formula:

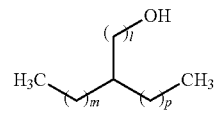

where l, m, and p are independently integers from 1-22, with the proviso that at least one of l, m, and p is an integer greater than 6, sometimes greater than 8. Isodecanol, Isoundecanol, Isolauryl alcohol, Isomyristyl Alcohol, 2-Hexyldecanol, Isostearyl Alcohol, Octyldodecanol, Isolignoceryl alcohol, Dodecylhexadecanol, Isotetradecyloctadecyl Alcohol, 2-Hexadecyleicosanol, and Isononanol, to name a few. In one embodiment, the polar oil comprises octyldodecanol.

Ester oils will typically be the esterification product of an acid of the form $R_a(COOH)_{1-2}$ with an alcohol of the form $R_b(OH)_{1-3}$ where $R_a$ and $R_b$ are each independently linear, branched, or cyclic hydrocarbon groups, optionally containing unsaturated bonds, and having from 1 to 30 carbon atoms, preferably from 2 to 30 carbon atoms, and more preferably, from 3 to 30 carbon atoms. These esters include, without limitation, esters of mono-acids with mono-alcohols, mono-acids with diols and triols, di-acids with mono-alcohols, and tri-acids with mono-alcohols.

Suitable fatty acid esters include, without limitation, butyl isostearate, butyl oleate, butyl octyl oleate, cetyl palmitate, ceyl octanoate, cetyl laurate, cetyl lactate, cetyl isononanoate, cetyl stearate, diisostearyl fumarate, diisostearyl malate, neopentyl glycol dioctanoate, dibutyl sebacate, di-$C_{12-13}$ alkyl malate, dicetearyl dimer dilinoleate, dicetyl adipate, diisocetyl adipate, diisononyl adipate, diisopropyl dimerate, triisostearyl trilinoleate, octodecyl stearoyl stearate, hexyl laurate, hexadecyl isostearate, hexydecyl laurate, hexyldecyl octanoate, hexyldecyl oleate, hexyldecyl palmitate, hexyldecyl stearate, isononyl isononanaote, isostearyl isononate, isohexyl neopentanoate, isohexadecyl stearate, isopropyl isostearate, n-propyl myristate, isopropyl myristate, n-propyl palmitate, isopropyl palmitate, hexacosanyl palmitate, octacosanyl palmitate, propylene glycol monolaurate, triacontanyl palmitate, dotriacontanyl palmitate, tetratriacontanyl palmitate, hexacosanyl stearate, octacosanyl stearate, triacontanyl stearate, dotriacontanyl stearate, stearyl octanoate, stearyl heptanoate, stearyl stearate, tetratriacontanyl stearate, triarachidin, tributyl citrate, triisostearyl citrate, tri-$C_{12-13}$-alkyl citrate, tricaprylin, tricaprylyl citrate, tridecyl behenate, trioctyldodecyl citrate, tridecyl cocoate, tridecyl isononanoate, glyceryl monoricinoleate, 2-octyldecyl palmitate, 2-octyldodecyl myristate, di(2-ethylhexyl) succinate, tocopheryl acetate, and the like.

Other suitable esters include those wherein R comprises a polyglycol of the form H—(O—CHR*—CHR*)$_n$— wherein R* is independently selected from hydrogen or straight chain alkyl, including methyl and ethyl, as exemplified by polyethylene glycol monolaurate.

Salicylates and benzoates are also contemplated to be useful esters in the practice of the invention. Suitable salicylates and benzoates include esters of salicylic acid or benzoic acid with an alcohol of the form ROH where R is a linear, branched, or cyclic hydrocarbon group, optionally containing unsaturated bonds, and having from 1 to 30 carbon atoms, preferably from 6 to 22 carbon atoms, and more preferably from 12 to 15 carbon atoms. Suitable salicylates include, for example, octyl salicylate and hexyldodecyl salicylate, and benzoate esters including $C_{12-15}$ alkyl benzoate, isostearyl benzoate, hexyldecyl benzoate, benzyl benzoate, and the like.

Other suitable oils include without limitation castor oil, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, avocado oil, camellia oil, macadamia nut oil, turtle oil, mink oil, soybean oil, grape seed oil, sesame oil, maize oil, rapeseed oil, sunflower oil, cottonseed oil, jojoba oil, peanut oil, olive oil, and combinations thereof. Other suitable oils include, without limitation, polyglyceryl diisostearate/IPDI copolymer, triisostearoyl polyglyceryl-3 dimer dilinoleate, polyglycerol esters of fatty acids, and lanolin, to name but a few.

The compositions may or may not be substantially anhydrous. Such compositions may comprise, for example, less than 1% by weight water. In other embodiments the composition are free of water by which is meant that no water is intentionally added to the composition other than trace amounts of water that may be associated with the various components as impurities or absorbed into the composition from the environment.

In one embodiment, the composition may or may not comprise volatile silicones. In other embodiments, the composition comprises less than 15%, less than 10%, or less than 5% by weight oil volatile silicone oil. In one embodiment, the composition does not comprise non-volatile silicone oils. In other embodiment, the composition comprises less than 15%, less than 10%, or less than 5% by weight non-volatile silicone oils. In one embodiment, the composition does not comprise wax. In other embodiment, the composition comprises less than 20%, less than 10%, or less than 5% by weight wax. In one embodiment, the composition comprises less than 1% by weight wax.

The compositions comprise a carbohydrate-based gelling agent, such as a cellulosic polymer. Suitable cellulosics include, without limitation, cellulose ethers such as methyl cellulose and ethyl cellulose and other derivatives including hydroxypropyl methyl cellulose (HPMC) and hydroxyethyl methyl cellulose (HEMC). Other cellulosics include cellulose acetate, carboxymethyl cellulose, and gel-forming gums (agar, calcium alginate, carrageenan, furcelleran, gellan, and pectin). In one embodiment, the gelling agent comprises ethyl cellulose. In one embodiment, the gelling agent consists of ethyl cellulose. In one embodiment, the gelling agent consists essentially of ethyl cellulose. In one embodiment, the gelling agent is water-insoluble. In one embodiment, the gelling agent is not water-dispersible.

The non-polar film-forming polymer is typically a polyolefin polymer. Such polyolefin polymers may be formed from the polymerization of monomers including ethylene, propylene, butylene, and other monomers of the form $(R)_2C=C(R)_2$ where R is independently at each occurrence from hydrogen, or a $C_{1-10}$ branched, straight chained, or cyclic aliphatic hydrocarbon (e.g., alkyl), or a phenyl group (i.e., styrene monomers and derivatives), or an alkyl-aryl group (e.g., benzyl), or a halogen (e.g., fluorine), or a group —(C=O)—O—R (where R is a defined above). In one embodiment, the olefin polymers may comprise aliphatic diene monomers. In one embodiment, the compound comprises optionally hydrogenated polycyclopentadiene monomers. The polyolefin polymers may be homopolymers, block copolymers, random copolymers, alternating copolymers of the like. In one embodiment, the non-polar film forming polymer component comprises polybutene. In one embodiment, the non-polar film forming polymer component consists of polybutene. In one embodiment, the non-polar film forming polymer component consists essentially of polybutene.

The compositions comprise a polyhydroxy-fatty acid where the fatty acid is a $C_8$-$C_{22}$ fatty acid, such as polyhydroxystearic acid. The polyhydroxystearic acid may be added directly to the cosmetic composition, or it may be first combined with the pigments in the form of a pigment pre-grind. The polyhydroxystearic acid may be mixed with the pigments under shear. It has been found that the gloss of the lipcolor is superior when the polyhydroxystearic acid is added to the pre-grind rather than directly to the cosmetic formulation with the balance of ingredients.

The composition may also comprise colorants such as dyes, pigments and lakes. As used herein, the term "pigments" embraces lakes and fillers such as talc, calcium carbonate, etc. Exemplary inorganic pigments include, but are not limited to, inorganic oxides and hydroxides such as magnesium oxide, magnesium hydroxide, calcium oxide, calcium hydroxides, aluminum oxide, aluminum hydroxide, iron oxides ($\alpha$-$Fe_2O_3$, $\gamma$-$Fe_2O_3$, $Fe_3O_4$, FeO) and iron hydroxides including red iron oxide, yellow iron oxide and black iron oxide, titanium dioxide, titanium lower oxides, zirconium oxides, chromium oxides, chromium hydroxides, manganese oxides, manganese hydroxides, cobalt oxides, cobalt hydroxides, cerium oxides, cerium hydroxides, nickel oxides, nickel hydroxides, zinc oxides and zinc hydroxides and composite oxides and composite hydroxides such as iron titanate, cobalt titanate and cobalt aluminate and the like. Preferably, the inorganic oxide particles may be selected from silica, alumina, zinc oxide, iron oxide and titanium dioxide particles, and mixtures thereof. In one embodiment, the pigments have a particle size from 5 nm to 500 microns, or from 5 nm to 250 microns, or from 10 nm to 100 microns. In some embodiments, the particle size (median) will be less than bout 5 microns or less than 1 micron.

Additional exemplary color additive lakes include, for example: D&C Red No. 19 (e.g., CI 45170, CI 73360 or CI 45430); D&C Red No. 9 (CI 15585); D&C Red No. 21 (CI 45380); D&C Orange No. 4 (CI 15510); D&C Orange No. 5 (CI 45370); D&C Red No. 27 (CI 45410); D&C Red No. 13 (CI 15630); D&C Red No. 7 (CI 15850:1); D&C Red No. 6 (CI 15850:2); D&C Yellow No. 5 (CI 19140); D&C Red No. 36 (CI 12085); D&C Orange No. 10 (CI 45475); D&C Yellow No. 19 (CI 15985); FD&C Red #40 (CI #16035); FD&C Blue #1 (CI #42090); FD&C Yellow #5 (CI #19140); or any combinations thereof.

In some embodiments, the composition does not comprise solvents in addition to the polar oils. In other embodiments, the composition may comprise added solvents. In one embodiment, the gel of the invention is added to an emulsion. The emulsion may be in the form of a water-in-oil, oil-in-water, water-in-silicone, silicone-in-water, polyol-in-silicone, silicone-in-polyol emulsion, etc. In one embodiment, the composition is anhydrous. In one embodiment, the composition may comprise an aqueous or ethanolic vehicle, silicone (e.g., cyclomethicone, dimethicone, etc.), hydrocarbon (e.g., petrolatum, isododecane, etc.), ester oil (isopropyl myristate, myristyl myristate, or the like. The vehicle may further comprise an emulsifier, gelling agent, structuring agent, rheology modifier (e.g., a thickener), film former, or the like. The vehicle may comprise from about 5% to about 99% by weight of the composition.

The compositions of the invention may include a cosmetically or dermatologically acceptable vehicle, which may be in the form of, for example, a serum, a cream, a lotion, a gel, or a stick, The vehicle may comprise an oil phase, an alcohol, a silicone phase or mixtures thereof. The vehicle may comprise vegetable oils; mineral oils; esters such as octyl palmitate, myristyl myristate, isopropyl myristate, and isopropyl palmitate; ethers such as dicapryl ether and dimethyl isosorbide; alcohols such as ethanol and isopropanol; fatty alcohols such as cetyl alcohol, cetearyl alcohol, and stearyl alcohol; volatile silicones such as cyclomethicones, silicone oils like dimethicone, amondimethicones, and dimethiconol; hydrocarbons such as mineral oil, petrolatum, and isoparaffins such as isooctane, isododecane (IDD), isohexadecane, and isoeicosane; and (hydrogentated)polyolefins such as polyisobutene; polyols such as propylene glycol, glycerin, butylene glycol, pentylene glycol and hexylene glycol; liposomes; waxes (animal, vegetable, or synthetic); or any combinations or mixtures of the foregoing.

The compositions may include natural or synthetic film-forming polymers. Suitable polymeric film formers include polyolefins, silicone polymers (e.g., dimethicones, dimethiconols, amodimethicones, etc.), (meth)acrylates, alkyl (meth)acrylates, polyurethanes, fluoropolymers, and silicone acrylates such as acrylates/dimethicone copolymers. Water-resistant film formers and oil-resistant film formers that can be used in the present compositions include, but are not limited to, one or more acrylics (acrylates), polyacrylates, urethanes, polyurethanes, polyesters, polysaccharides, polyolefins, polyamides, polyimides, polyethylenes, polyalkyls, polyols, polystyrenes, polyethers, polynitriles, cellulosics, proteins, triglycerides, polyamino acids, silicone polymers and resins, esters derived from rosin, epoxy resins, shellacs, latexes, or any combinations thereof. In some embodiments, it may be desirable to add a hydrophilic or water-soluble film former (e.g., cellulosics, polysaccharides, polyquaterniums (such as polyquaternium-37 (INCI), etc.) to the composition to improve spreading, emulsion stability, aesthetic look and feel, etc. Fluorinated polymers, such as those having the INCI name polyperfluoromethylisopropyl ether, may be useful to modify slip and feel of the composition. Fluorinated polymers are supplied by Solvey Solexis, for example, under the trade name FOMBLIN HC. Sucrose acetate isobutyrate (INCI) supplied by Eastman Chemical and glycerol rosinate (INCI) sold under the trade name SylvaGum RE 85K by Arizona Chemical are also contemplated film formers.

The cosmetic compositions of the invention may optionally include one or more agents that provide or enhance shine. Shine enhancing agents will typically have a refractive index greater than about 1.4, preferably greater than about 1.5 when measured as a film at 25° C. Suitable shine enhancing agents include without limitation, polyols, fatty esters, silicone phenylpropyldimethylsiloxysilicate, polybutene, polyisobutene, hydrogenated polyisobutene, hydrogenated polycyclopentadiene, propyl phenyl silsesquioxane resins; lauryl methicone copolyol, perfluorononyl dimethicone, dimethicone/trisiloxane, methyl trimethicone, and combinations thereof. In one embodiment, the composition will comprise a shine-enhancing agent in an amount from about 0.1% to about 10% by weight, based on the total weight of the composition.

The compositions may further include an emulsifier. The amount of emulsifier will typically be from about 0.001 to about 10% by weight, but preferably will range from about 0.01 to about 5% by weight, and most preferably about 0.1 to about 1% by weight, based upon the total weight of the composition. The emulsifier may be ionic, zwitterionic, or nonionic. Suitable emulsifiers include those of the polyethoxylated type (e.g., polyoxyethylene ethers or esters), polydiorganosiloxane-polyoxyalkylene block copolymers (e.g., dimethicone copolyol), Steareth-20, Steareth-21, fatty alcohols (e.g., Cetearyl Alcohol), Polyoxethylene sorbitan fatty acid esters (i.e., polysorbates), and Hydrogenated Castor Oil, to name a few. Additional emulsifiers are provided in the INCI Ingredient Dictionary and Handbook 11th Edition 2006, the disclosure of which is hereby incorporated by reference.

The composition may also comprise humectants such as polyols (e.g., glycols), including without limitation, glycerin, propylene glycol, ethoxydiglycol, butylene glycol, pentylene glycol, hexylene glycol, caprylyl glycol, and the like. These will typically be added in amount from about 0.001 to about 5% by weight when present.

A sunscreen may be included to protect the skin from damaging ultraviolet rays. In an illustrative embodiment of the present disclosure, the sunscreen provides both UVA and UVB protection, by using either a single sunscreen or a combination of sunscreens. Among the sunscreens that can be employed in the present compositions are avobenzone, cinnamic acid derivatives (such as octylmethoxy cinnamate), octyl salicylate, oxybenzone, octocrylene, titanium dioxide, zinc oxide, or any mixtures thereof. The sunscreen may be present from about 1 wt % to about 30 wt % of the total weight of the composition.

Other suitable components include those agents that provide a prophylactic or therapeutic benefit to skin. Particular mention may be made of alpha-hydroxy acids, beta hydroxyl acids, ascorbic acid or Vitamin C and derivatives thereof (e.g., $C_1$-$C_8$ esters thereof); retinoids such as retinol (Vitamin A) and the esters thereof (e.g., $C_1$-$C_8$ esters, such as palmitate), retinoic acid and the derivatives thereof, hyaluronic acid, chemical sun screens useful in the cosmetic field including any UVA and UVB filter useful in the cosmetic field including mixtures thereof and blends with physical filters including, but not limited to metal oxide particles such as titanium oxides and/or zinc oxides. Additional benefit agents include botanicals, thiodipropionic acid (TDPA) and esters thereof; (e.g., retinoic acid, all-trans-retinoic acid, retinaldehyde, retinol, and retinol esters such as acetates or palmitates, and others); alpha-hydroxy acids (e.g., glycolic acid), beta-hydroxy acids (e.g., salicylic acid and salicylates); exfoliating agents (e.g., glycolic acid, 3,6, 9-trioxaundecanedioic acid, etc.), depigmenting agents (e.g., hydroquinone, kojic acid, etc.) estrogen synthetase stimulating compounds (e.g., caffeine and derivatives); compounds capable of inhibiting 5 alpha-reductase activity (e.g., linolenic acid, linoleic acid, finasteride, and mixtures thereof); antioxidants (e.g., BHT, ascorbic acid, sodium ascorbate, ascorbyl palmitate, beta-carotene, thiodipropionic acid, vitamin E, etc.), barrier function enhancing agents (e.g., ceramides, glycerides, cholesterol and its esters, alpha-hydroxy and omega-hydroxy fatty acids and esters thereof, etc.); collagenase inhibitors; and elastase inhibitors; to name a few. These benefit agents will typically be present, if at all, in amounts between about 0.001% and about 10% by weight of the composition.

Other additives include: vitamins, such as tocopherol and ascorbic acid; vitamin derivatives such as ascorbyl monopalmitate, tocopheryl acetate, and Vitamin E palmitate; thickeners such as hydroxyalkyl cellulose, carboxymethylcellulose, carbomers, and vegetable gums such as xanthan gum; gelling agents (e.g., silicone T-resins), such as esterterminated polyester amides; structuring agents; metal chelating agents such as EDTA or salts thereof; and pH adjusters (citric acid, ethanolamine, sodium hydroxide, etc.). The composition may optionally comprise other components known to those skilled in the art including, but not limited to, moisturizers, minerals, viscosity and/or rheology modifiers, anti-acne agents, insect repellents, skin cooling compounds, skin protectants, lubricants, fragrances, preservatives, stabilizers, and mixtures thereof. In addition to the foregoing, the cosmetic compositions of the invention may contain any other compound for the treatment of skin disorders.

The compositions typically comprises a preservative or anti-microbial agent, for example, methylchloroisothiazolinone, methylisothiazolinone, methylparaben, propylparaben, phenoxyethanol, or caprylyl glycol.

In some embodiments, the compositions are capable of delivering high gloss when applied to the lips. By the term "high gloss" is meant an 85 degree gloss value greater than about 70, greater than about 75, greater than about 80, greater than about 85, or greater than about 90 or even higher.

The cosmetic composition may be capable of imparting durable shine to the lips, by which is meant that the film has high gloss over a prolonged period of time (e.g., the gloss diminishes by less than 25% over a period of one hour or more). In one embodiment, the composition loses less than 10% of its gloss over a 1 hour period. In one embodiment, the composition loses less than 10% of its gloss over a 2 hour period. In one embodiment, the composition loses less than 10% of its gloss over a 3 hour period. The gloss can be measured, for example, using a Bossa Nova gloss analyzer.

The composition can be applied as often as necessary to impart the desired cosmetic finish, color or appearance to the lip and/or skin. The lip coloring and lip gloss products preferably imparts a moist feel to the lips. The present invention affords lip coloring and lip gloss products with creamy, smooth and even application. After application, the products dry to an even film on the lips and resist transfer and wear from abrasion. These performance benefits are due to the inclusion of both a water-resistant and an oil-resistant film former. Erosion from drinking, eating, smoking, talking and the like is significantly reduced. The need for reapplication of product is significantly reduced. Typically, a conventional lip gloss will not have such long wear properties.

A composition according to the invention can be expected to achieve long wear, comfort, and gloss, and remain on the lips for a long-wear period such as from about 1 to about 12 hours, period from about 2-8 hours, or from about 3-6 hours. In various embodiments gloss is retained for at least 1 hour, at least 2 to 4 hours, at least 2 to 6 hours, or at least 8 hours.

A variety of evaluation methods of transfer resistance and long wearing properties are known in the cosmetic arts, such as in dry blot, oil blot, and rub tests. For example, U.S. Pat. No. 6,071,503 discloses various methods of evaluating cosmetic properties, the disclosure of which is hereby incorporated by reference.

In one embodiment, the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, § 201(i).

Example 1

Gloss and Color Measurements: L*a*b color scale measurements with and without PHA.

Various formulations were prepared, either with or without the addition of polyhydroxysteric acid (PHA), and the color attributes of the formulations were assessed. Ingredients for formulations 1, 2, 3, 7, 8, 9, and 10 are presented below in Table 1.

TABLE 1

| Ingredient | #1 | #2 | #3 | #7 | #8 | #9 | #10 |
|---|---|---|---|---|---|---|---|
| | \multicolumn{7}{c}{Amount (%)} | | | | | | |
| Ethylcellulose/Octyldodecanol Gel | 35 | 35 | 0 | 30 | 30 | 0 | 0 |
| Octyldodecanol | 35 | 35 | 53 | 35 | 35 | 48 | 48 |
| Grind TTB Treated Pigments (Red iron oxide)* | 24 | 25 | 24 | 0 | 0 | 0 | 0 |
| Grind TTB Treated Pigment (Red 7)* | 0 | 0 | 0 | 24 | 25 | 24 | 25 |
| Beeswax | 0 | 0 | 17 | 0 | 0 | 17 | 17 |
| Polyhydroxystearic acid (PHA)* | 1 | 0 | 1 | 1 | 0 | 1 | 0 |
| Polybutene | 5 | 5 | 5 | 10 | 10 | 10 | 10 |

*The pigments in the samples containing polyhydroxystearic acid are pregrinds in accordance with the invention.

Color attributes of the above formulations were assessed, and are presented below in Tables 2 and 3.

TABLE 2

| Sample | PHA addition | Wax addition | L | a | b | Delta E (compared to sample 1) | Gloss |
|---|---|---|---|---|---|---|---|
| 1 | Yes | No | 39.22 | 39.42 | 23.43 | | 80.8 |
| 2 | No | No | 38.44 | 37.66 | 20.38 | 3.55 | 80.3 |
| 3 | Yes | Yes | 42.56 | 36.06 | 19.58 | 6.16 | 19.90 |

| Sample | PHA addition | Wax addition | L | a | b |
|---|---|---|---|---|---|
| 7 | Yes | No | 30.01 | 59.86 | 51.01 |
| 8 | No | No | 29.84 | 59.04 | 50.63 |
| 9 | Yes | No | 31.60 | 59.14 | 50.56 |
| 10 | No | Yes | 32.47 | 57.25 | 44.88 |

The data above in Tables 2 and 3 demonstrate that the color attributes tested on the various formulations are superior when PHA is part of the formulation.

Example 2

Gloss and Color Measurements: L*a*b measurements of formulations prepared by different procedures A formulation containing Parts A, B and C was prepared as shown in Table 4 below.

TABLE 4

| Ingredient | Weight |
|---|---|
| Part A | |
| Polybutene | 20.000 g |
| Hydrogenated polyisobutene | 20.000 g |
| Ethylcellulose gel/octyldodecanol | 5.000 g |
| Part B | |
| Titanium dioxide/titanate treated | 24.600 g |
| Iron Oxides-Red Isopropyl Titinate | 11.100 g |
| D&C Red No.7 | 3.700 g |

TABLE 4-continued

| Ingredient | Weight |
|---|---|
| Brown umber oxide/titanate treated | 7.050 g |
| Cosmetic red oxide/titanate treated | 1.350 g |
| Iron oxide black/titanate treated | 0.200 g |
| Iron oxide yellow/titanate treated | 1.750 g |
| FD&C blue No.1 | 0.250 g |
| Part C | |
| polyhydroxystearic acid | 5.000 g |

Two different samples were prepared containing Parts A, B, and C, but with different procedures. The sample made by Procedure 1 was such that Parts A, B, and C were mixed together, and then passed through 3 Roller Ball Mill. The sample made by Procedure 2 was such that Parts A and B were mixed together, and the mixture then passed through 3 Roller Ball Mill. Following this, Part C was added, and missed with the previously milled product.

To assess the differences in color attributes for the samples prepared by Procedure 1 and Procedure 2, the following methodology was employed. 6, 3-mil drawdowns of each product were applied to white *lenta* cards. The samples were then allowed to dry for 1 hour. A Minolta hand-held spectrophotometer, model CM-2600d was used to take 3 L*a*b* measurements per drawdown (18 measurements per sample). The results of this test are presented below in Table 5.

TABLE 5

| | Average | | | |
|---|---|---|---|---|
| Sample | L* (D65) | A* (D65) | B* (D65) | |
| Procedure 1 | 38.08 | 22.34 | 8.34 | |
| Procedure 2 | 34.14 | 29.50 | 3.43 | |
| Delta | 3.94 | −7.16 | 4.91 | Delta E = 9.53 |

The delta value is the difference between the two products, and the overall color difference is defined as Delta $E=((Delta\ L)^2+(Delta\ a)^2+(Delta\ b)^2)^{1/2}$. If the value of Delta E is >|1| then there is a perceptible change in color. The results in Table 5 above demonstrate, therefore, that there is a perceptible difference in the overall color when comparing the sample prepared with Procedure 1 to the sample prepared with Procedure 2, such that the color development is significantly greater after Procedure 1.

Example 3

Gloss and Color: L*a*b measurements of pigment grinds and lipsticks with and without PHA Two different pigment grinds were prepared, as show in in Table 6 below. Grind 1 contains PHA, whereas Grind 2 does not contain PHA.

TABLE 6

| Ingredient | Grind 1 (weight) | Grind 2 (weight) |
|---|---|---|
| Octyldodecanol | 12.5 g | 12.5 g |
| Polyhydroxystearic acid | 0.85 g | 0 g |
| Castor oil preserved | 5.70 g | 5.70 g |
| Iron Oxide Red coated with triethoxycaprylyl silane | 2.50 g | 2.50 g |
| Titanium dioxide-triethoxycaprylylsilane | 2.70 g | 2.70 g |

TABLE 6-continued

| Ingredient | Grind 1 (weight) | Grind 2 (weight) |
|---|---|---|
| Iron oxide yellow coated with trietoxycaprylyl silane | 4.30 g | 4.30 g |
| D&C red 7 lake/triethoxycaprylylsylane | 1.96 g | 1.96 g |

The two pigment grinds were then used to make two different lipstick formulations, one containing Grind 1, and one containing Grind 2, as shown in Table 7 below.

TABLE 7

| Ingredient | Lipstick 1 (weight) | Lipstick 2 (weight) |
|---|---|---|
| Grind 1 | 30 g | 0 g |
| Grind 2 | 0 g | 30 g |
| Polyethylene wax | 2.50 g | 2.50 g |
| Candelilla wax | 1.50 g | 1.50 g |
| Ozokerite 170-d | 4.50 g | 4.50 g |
| Ethylcellulose gel/octyldodecanol | 15.00 g | 15.00 g |
| Ethylhexyl-methoxycinnamate | 5.00 g | 5.00 g |
| Benzophenone-3 (oxybenzone) | 3.00 g | 3.00 g |
| Polybutene | 15.00 g | 15.00 g |
| Neopentyl glycol dicaprate | QS | QS |

To assess the difference in color attributes between the two grinds and between the two lipsticks prepared using Grind 1 and Grind 2, L*a*b* measurements were taken using the methodology described above for Example 2. The results of this test are presented below in Table 8.

TABLE 8

| | Average | | | |
|---|---|---|---|---|
| | L* (D65) | a* (D65) | b* (D65) | |
| Grind 1 | 36.034 | 34.88 | 9.346 | |
| Grind 2 | 35.736 | 33.988 | 7.404 | |
| Delta | −0.298 | −0.892 | −1.942 | Delta E = 2.327196 |
| Lipstick 1 | 40.79667 | 33.89167 | 12.08167 | |
| Lipstick 2 | 39.492 | 33.876 | 8.86 | |
| Delta | −1.30467 | −0.01567 | −3.22167 | Delta E = 6.040768 |

The Delta values represent the difference between the products compared, according to the formula presented above in Example 2. As shown in Table 8, the Delta E values for the compared grinds and for the compared lipsticks are both greater than 1, which indicates that there was a perceptible difference between the grinds compared and between the lipsticks compared. Therefore, there is a difference in the overall color between Grind 1 and Grind 2, and between Lipstick 1 and Lipstick 2. The Delta b* values between Grind 1 and Grind 2, and between Lipstick 1 and Lipstick 2 are greater than 1, which indicates that Grind 1 and Lipstick 1 have more yellow than Grind 2 and Lipstick 2.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described therein will become apparent to those skilled in the art from the foregoing description. Such modifications are also intended to fall within the scope of the appended claims. All publications cited herein are incorporated by reference in their entirety.

What is claimed:

1. A method for providing a long-wearing durable film on the lips comprising applying to the lips a composition comprising:
   (1) a polar oil comprising a fatty alcohol;
   (2) a cellulose ether capable of forming a gel with said polar oil;
   (3) a non-polar film-forming polyolefin polymer;
   (4) polyhydroxystearic acid; and
   (5) pigments;
   to form a durable film on the lips characterized by high gloss and transfer-resistance, wherein (1)-(5) were mixed under shear; and
   wherein said composition is characterized by greater color development than an otherwise identical composition in which (4) was added after (1)-(3) and (5) were mixed under shear; and
   wherein the composition comprises less than 1% by weight wax.

2. The method according to claim 1, wherein said polar oil further comprises an ester oil.

3. The method according to claim 1, wherein said polar oil comprises octyldodecanol.

4. The method according to claim 1, wherein said cellulose ether is ethyl cellulose.

5. The method according to claim 1, wherein said polyolefin is polybutene.

6. The method according to claim 1, wherein said cellulose ether comprises from about 1% to about 2.5% by weight and said polar oil comprises from about 5% to about 35% by weight of said composition.

7. The method according to claim 1, wherein said composition is substantially free of water.

* * * * *